(12) United States Patent
Lee et al.

(10) Patent No.: US 9,916,504 B2
(45) Date of Patent: Mar. 13, 2018

(54) USER TERMINAL AND METHOD OF PROVIDING INFORMATION TO A USER THEREOF

(71) Applicant: Samsung Electronics Co., Ltd., Suwon-si (KR)

(72) Inventors: Kang-min Lee, Hwaseong-si (KR); Jun-ho Koh, Suwon-si (KR); Byeong-hoon Kwak, Uiwang-si (KR); Sung-chan Kim, Suwon-si (KR); Yang-wook Kim, Hwaseong-si (KR); Chang-han Kim, Suwon-si (KR); Hyun-jung Kim, Suwon-si (KR); In-hak Na, Yongin-si (KR); Kang-jin Yoon, Seoul (KR); Yong-chan Lee, Seoul (KR); Jae-ho Jung, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 67 days.

(21) Appl. No.: 15/019,028

(22) Filed: Feb. 9, 2016

(65) Prior Publication Data

US 2016/0232408 A1    Aug. 11, 2016

(30) Foreign Application Priority Data

Feb. 10, 2015  (KR) .................. 10-2015-0020070

(51) Int. Cl.
  *G06K 9/00* (2006.01)
  *G06F 3/048* (2013.01)
  *A61B 5/00* (2006.01)

(52) U.S. Cl.
  CPC ........ *G06K 9/00617* (2013.01); *A61B 5/0077* (2013.01); *A61B 5/7435* (2013.01); *G06F 3/048* (2013.01); *G06K 9/00604* (2013.01)

(58) Field of Classification Search
  CPC ........... G06K 9/00617; G06K 9/00604; G06K 9/00597; A61B 5/0077; A61B 5/7435; G06F 3/048
  See application file for complete search history.

(56) References Cited

U.S. PATENT DOCUMENTS

| | | | |
|---|---|---|---|
| 5,291,560 A | 3/1994 | Daugman | |
| 8,831,557 B2 | 9/2014 | Jung et al. | |
| 2006/0072793 A1* | 4/2006 | Determan | G06K 9/00335 382/117 |
| 2016/0180070 A1* | 6/2016 | Shi | G06K 9/00597 726/18 |

FOREIGN PATENT DOCUMENTS

| | | |
|---|---|---|
| CN | 102429637 | 5/2012 |
| JP | 08504979 A | 5/1996 |

(Continued)

OTHER PUBLICATIONS

Martyn et al "Pupil cycle time: a simple way of measuring an autonomic reflex", Journal of Neurology, Nerosurgery, and Psychiatry 1986; 49:771-774.*

(Continued)

*Primary Examiner* — Yon Couso
(74) *Attorney, Agent, or Firm* — McAndrews, Held & Malloy, Ltd.

(57) ABSTRACT

A user terminal and a providing method thereof are provided. The method includes acquiring an iris image, determining a capturing condition of the iris image, converting the acquired iris image to an iris code and performing iris recognition by comparing the converted iris code with an iris code corresponding to a determined capturing condition among pre-registered iris codes, determining a physical condition of a user who is subject to the iris recognition on the basis of an iris recognition matching rate being within a preset range, and providing a determined physical condition result.

20 Claims, 33 Drawing Sheets

(56) References Cited

FOREIGN PATENT DOCUMENTS

| JP | 2007029333 A | 2/2007 |
|---|---|---|
| KR | 100376415 | 3/2003 |
| KR | 1020060082195 | 7/2006 |
| KR | 1020080077886 | 8/2008 |
| KR | 10-2008-0109695 A | 12/2008 |
| KR | 10-2009-0065716 A | 6/2009 |
| KR | 101160681 | 6/2012 |
| KR | 101160681 B1 | 6/2012 |

OTHER PUBLICATIONS

Int'l Search Report for PCT/KR2016/001362 dated May 18, 2016.
Written Opinion for PCT/KR2016/001362 dated May 18, 2016.
Extended European Search Report for Appln. No. 16749457.4 dated Dec. 6, 2017 (10 pages).
G Durgadevi et al: "Disease Identification in Iris Using Gabor Filter". International Journal of Engineering and Computer Science ISSN. Apr. 1, 2014 (Apr. 1, 2014). pp. 2319-72425396. XP055429470. Retrieved from the Internet:http://www.ijecs.in/issue/v3-i4/27ijecs.pdf [retrieved on Nov. 28, 2017] * sections I-IV * * abstract; figures 1-3.
Sivasankar K et al: "FCM based iris image analysis for tissue imbalance stage identification". Emerging.Trends in Science. Engineering and Technology (INCOSET). 2012 International Conference On IEEE. Dec. 13, 2012 (Dec. 13, 2012). pp. 210-215. XP032396060. DOI: 10.1109/Incoset.2012.6513907 ISBN: 978-1-4673-5141-6 * sections I-IV * * abstract; figures 1-5.
Hareva David Habsara et al: "The smart device for healthcare service: Iris diagnosis application", 2013 Eleventh International Conference on ICT and Knowledge Engineering, IEEE, Nov. 20, 2013 (Nov. 20, 2013), pp. 1-6, XP032574086, ISSN: 2157-0981, DOI: 10.1109/Ictke.2013.6756277 ISBN: 378-1-4799-8025-3 [retrieved on Mar. 4, 2014] * sections I-VI * * abstract; figures 1-5.

* cited by examiner

USER TERMINAL AND METHOD OF PROVIDING INFORMATION TO A USER THEREOF

RELATED APPLICATION(S)

This application claims priority from Korean Patent Application No. 10-2015-0020070, filed on Feb. 10, 2015, in the Korean Intellectual Property Office, the disclosure of which is incorporated herein by reference in its entirety.

BACKGROUND

Apparatuses and methods consistent with exemplary embodiments relate to a user terminal and a providing method thereof, and more particularly, to a user terminal capable of determining a physical condition of a user, and a providing method thereof.

As a variety of personal information or content information is stored in personal user terminals, demands on security for the user terminals have increased. The password input method is used for securing the user terminals in the related art, but various authentication methods such as fingerprint recognition, voice recognition, or iris recognition have been introduced in recent years.

For iris recognition in the user terminals, an image of a portion of a face including an eye of the user needs to be captured. Therefore, there is a need for a method of performing iris recognition by capturing an image of the eye of the user and simultaneously using the image acquired for iris recognition in various ways.

SUMMARY

Various exemplary embodiments relate to a user terminal capable of allowing a user to receive feedback for a physical condition of the user while the user is subject to iris recognition, and a providing method thereof.

According to an aspect of an exemplary embodiment, there is provided a method including acquiring an iris image, determining a capturing condition of the iris image, converting the acquired iris image to an iris code and performing iris recognition by comparing the converted iris code with an iris code corresponding to a determined capturing condition among pre-registered iris codes, determining a physical condition of a user who is subject to the iris recognition on the basis of an iris recognition matching rate being within a preset range, and providing a determined physical condition result.

The determining of the capturing condition may include determining the capturing condition includes determining at least one of an illumination value of an environment in which the iris image is captured, a distance between the user and the user terminal, a shape of an eye in the iris image of the user, and a neighboring color of the user in the capturing of the iris image.

The method may further include matching information for the iris image to the capturing condition of the iris image and storing a matching result, wherein determining the physical condition includes acquiring information for a pre-stored iris image corresponding to the determined capturing condition among pre-stored capturing conditions and determining the physical condition based on the information for the pre-stored iris image.

The determining of the physical condition may include determining the physical condition by removing an eyelid region and a reflection region in the iris image and comparing the iris image with the eyelid region and the reflection region removed and a pre-stored iris image.

The iris recognition success rate within the preset range may refer to an iris recognition matching rate within a range in which the iris recognition is deemed successful and as a result the user terminal is unlocked.

The providing may further include displaying a user interface (UI) configured to provide the determined physical condition result in response to unlocking the user terminal through success of the iris recognition.

The UI configured to provide the physical condition result may include at least one of a UI configured to notify the user of a health problem, a UI configured to notify the user of a hospital located within a preset distance from the user terminal, and a self-diagnosis UI.

The providing of the physical condition result may further include displaying a self-diagnosis UI configured to allow the user to perform self-diagnosis on the user, providing a result of the self-diagnosis performed through the self-diagnosis UI, and displaying a UI configured to notify the user of a hospital located within a preset distance from the user terminal in response to the result of the self-diagnosis.

The performing of the iris recognition may further include measuring a pupil cycle time (PCT) of the user, and determining the physical condition includes determining the physical condition of the user in response to the measured pupil cycle time not being within a range of a preset pupil cycle time.

The acquiring of the iris image may further include capturing a region including an eye of the user, and providing the determined physical condition result further includes displaying the determined physical condition with a captured image of an eye of the user.

According to an aspect of an exemplary embodiment, there is provided a user terminal including an iris image acquisition unit configured to acquire an iris image, a storage unit configured to store iris codes and capturing conditions, a controller configured to determine a capturing condition of the acquired iris image, convert the acquire iris image to an iris code, perform iris recognition by comparing the converted iris code with an iris code corresponding to the determined capturing condition among the iris codes pre-registered in the storage unit, and determine a physical condition of a user who is subject to the iris recognition based on an iris recognition result in response to an iris recognition matching rate being within a preset range as the iris recognition result, and an output unit configured to provide a determined physical condition result.

The user terminal may further include a detector including at least one of a plurality of sensors and a camera, wherein the controller determines the capturing condition by determining at least one among an illumination value of an environment in which the iris image is captured, a distance between the user and the user terminal, a shape of an eye in the iris image of the user, and a neighboring color of the user in the capturing of the iris image through the detector.

The controller may control the storage unit to match information for the iris image to the determined capturing condition of the iris image and store a matching result, and the controller acquires information for a pre-stored iris image corresponding to the determined capturing condition among the capturing conditions pre-stored in the storage unit and determines the physical condition based on the information for the pre-stored iris image.

The controller may determine the physical condition by removing an eyelid region and a reflection region in the iris image and comparing the iris image with the eyelid region and the reflection region removed and a pre-stored iris image.

The iris recognition matching rate within the preset range refers to an iris recognition matching rate within a range in which the iris recognition is deemed successful and, hence, unlocking the user terminal.

The output unit may further include a display, and the controller may control the display to display a user interface (UI) configured to provide the determined physical condition result in response to unlocking the user terminal through success of the iris recognition.

The UI configured to provide the determined physical condition result may include at least one of a UI configured to notify the user of a health problem, a UI configured to notify the user of a hospital located within a preset distance from the user terminal, and a self-diagnosis UI.

The output unit may further include a display, and the controller may control the display to display a self-diagnosis UI configured to allow the user to perform self-diagnosis on the user, provide a result of the self-diagnosis performed through the self-diagnosis UI, and display a UI configured to notify the user of a hospital located within a preset distance from the user terminal in response to the result of the self-diagnosis.

The controller may measure a pupil cycle time (PCT), and determine the physical condition of the user in response to the measured pupil cycle time being not within a range of a preset pupil cycle time.

The iris image acquisition unit may further include an iris capturing module, and the controller may control the iris capturing module to acquire the iris image by capturing a region including an eye of the user, and control the output unit to provide the physical condition result by displaying the determined physical condition with a captured image of an eye of the user.

According to various exemplary embodiments, the user may be subject to iris recognition through a user terminal and receive feedback for a physical condition.

Additional aspects and advantages of the exemplary embodiments are set forth in the detailed description, and will be obvious from the detailed description, or may be learned by practicing the exemplary embodiments.

BRIEF DESCRIPTION OF THE DRAWINGS

The above and/or other aspects of the present disclosure will be made more apparent by descriptions of various exemplary embodiments with reference to the accompanying drawings, in which.

DETAILED DESCRIPTION

Exemplary embodiments are described herein with reference to illustrations of exemplary embodiments. Thus, it should not be construed that all embodiments are limited to the particular shapes of regions illustrated herein. Various embodiments may be embodied in different forms and it will be appreciated by those of ordinary skill in the art that changes may be made in these exemplary embodiments without departing from the principles and spirit of the inventive concept, some scope of which is defined by the claims and their equivalents. Also, well-known functions or constructions are not described in detail since they would obscure the description of the embodiments with unnecessary detail.

It will be understood that, although the terms first, second, etc. may be used herein in reference to elements of the disclosure, such elements should not be construed as being limited by these terms. The terms are used only to distinguish one element from other elements.

The terminology used herein to describe embodiments of the disclosure is not intended to limit the scope of the disclosure. The articles "a," "an," and "the" are singular in that they have a single referent; however, the use of the singular form in the present document should not preclude the presence of more than one referent. In other words, elements of the disclosure referred to in the singular may number one or more, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

In exemplary embodiments, "module" or "unit" may perform at least one function or operation, and may be implemented with hardware, software, or a combination thereof. In some cases, a "plurality of modules" or "plurality of units" may be implemented with software executed by one or more processors.

Figure 1:
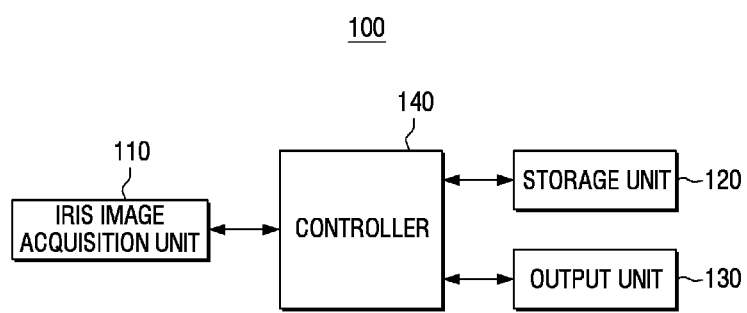
FIG. 1 is a schematic block diagram illustrating a configuration of a user terminal according to an exemplary embodiment.

FIG. 1 is a schematic block diagram illustrating a configuration of a user terminal 100 according to an exemplary embodiment. As illustrated in FIG. 1, the user terminal 100 may include an iris image acquisition unit 110, a storage unit 120, an output unit 130, and a controller 140.

The iris image acquisition unit 110 may be configured to acquire an iris image of the user. The iris image acquisition unit 110 may acquire the iris image by capturing the iris of the user or receiving an iris image of the user from another device or server.

The storage unit 120 may be configured to store various program modules required in the user terminal 100.

The storage unit 120 may store an iris code and a capturing condition. For example, the storage unit 120 may store the iris code corresponding to at least one user. In this example, the iris code may be data in which an iris region of the user is normalized to a rectangular shape, and may be used in iris recognition. A method of acquiring the iris code will be described in detail later.

If the iris recognition is successful, the iris code stored in the storage unit 120 may be updated.

The storage unit 120 may store image capturing information such as, for example, illumination value (brightness) of an environment in which the iris image is captured, distance between the user whose iris image is captured and the user terminal 100, eye shape of the user whose iris image is captured, and/or a neighboring color of the user whose iris image is captured. Herein, the neighboring color includes at least one of skin color, color of sclera and color of other part of the eye.

The output unit 130 may be configured to output a variety of content provided by the user terminal 100. For example, the output unit 130 may output a physical condition assessment of the user in various forms.

The controller 140 may control an overall operation of the user terminal 100. For example, the controller 140 may determine the capturing conditions of the iris image and convert the iris image to an iris code. The controller 140 may perform iris recognition by comparing the converted iris code with a stored iris code, where the stored iris code was found by searching for capturing condition similar to the determined capturing condition. The iris recognition matching rate (or iris recognition success rate) between the converted iris code and the stored iris code may determine whether it is a successful recognition. The iris recognition matching rate may be, for example, compared to a threshold rate to determine whether the iris recognition is successful. Successful iris recognition may result in unlocking the user terminal so that the user can have access to the user terminal.

The controller 140 may also determine a physical condition of the user who is subject to the iris recognition based on the iris recognition matching rate. If the iris recognition matching rate falls within a preset range(s), that may indicate certain physical conditions.

The controller 140 may also control a pupil cycle time (PCT) of the user to be measured. If the measured pupil cycle time is not within a preset pupil cycle time range, the controller 140 may determine the physical condition of the user who is subject to the iris recognition.

When the iris image is acquired through the iris image acquisition unit 110, and the acquired iris image is registered, the controller 140 may control the storage unit 120 to correlate the iris image information to the capturing condition of the iris image and store the corresponding information.

The iris image information may include the pupil cycle time measured in the iris image acquisition and the iris code to which the iris image is converted in addition to the iris image.

Figure 2:
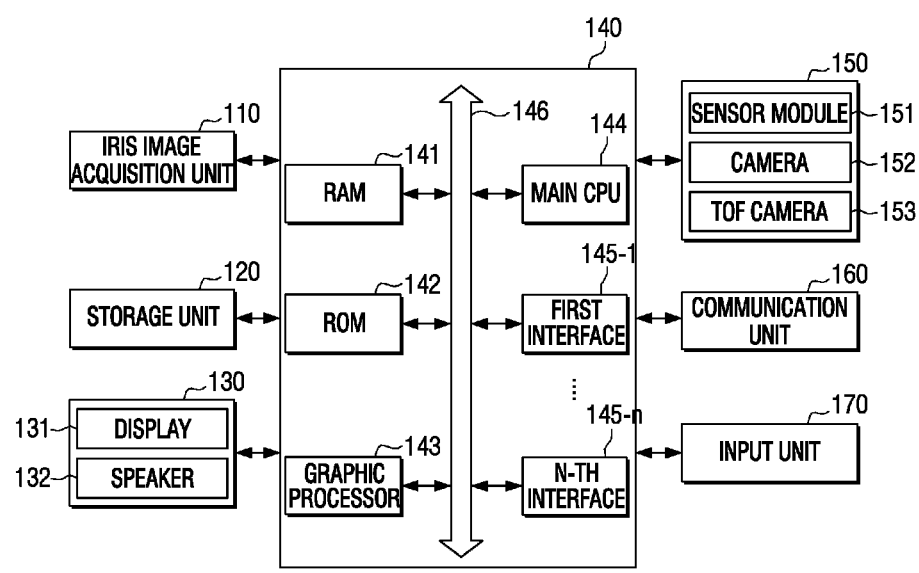
FIG. 2 is a block diagram illustrating a configuration of a user terminal according to an exemplary embodiment.

Hereinafter, the configuration of the user terminal 100 will be described in detail with reference to FIG. 2. As illustrated in FIG. 2, the user terminal 100 may further include a detector 150, a communication unit 160, and an input unit 170 in addition to the iris image acquisition unit 110, the storage unit 120, the output unit 130, and the controller 140.

The iris image acquisition unit 110 may be configured to acquire an iris image. For example, the iris image acquisition unit 110 may include a camera. In this example, the iris image acquisition unit 110 may acquire the iris image by capturing the user located in front of the user terminal 100 through the camera including a mirror type infrared pass filter called a cold mirror.

The storage unit 120 may store various modules configured to be executed by the user terminal 100. For example, the storage unit 120 may store software including a base module, a sensing module, a communication module, a presentation module, a web browser module, and a service module. The base module may refer to a basic module that processes signals transmitted from hardware included in the user terminal 100 and transmits the processed signals to an upper layer module. The sensing module may be a module that collects information from various sensors, and analyzes and manages the collected information. The sensing module may include a facial recognition module, a voice recognition module, a motion recognition module, a near field communication (NFC) recognition module, and the like. The presentation module may be a module that forms a display screen. The presentation module may include a multimedia module that reproduces multimedia content and outputs the reproduced content, and a UI rendering module that performs UI and graphic processing. The communication module may be a module configured to perform communication with external apparatuses. The web browser module may refer to a module that performs web browsing and accesses a web server. The service module may be a module including various applications for providing a variety of service.

The storage unit 120 may include the various program modules as described above. However, according to the kind and characteristic of the user terminal 100, the various program modules may be modified, portions of the various program modules may be omitted, or other modules may be added to the various program modules. For example, if the user terminal 100 is implemented as a tablet personal computer (PC), a position determination module for determining a global positioning system (GPS)-based position may be further included in the base module, and a sensing module for detecting an action of the user may be further include in the sensing module.

The storage unit 120 may store an iris code and its capturing condition. For example, the storage unit 120 may store an iris code corresponding to at least one user. The iris code may be data in which the iris region of the user may be normalized to a rectangular shape, and may be used for iris configuration. If the iris recognition is successful, the iris code stored in the storage unit 120 may be updated through control of the controller 140.

The storage unit 120 may store illumination value of an environment in which the iris image is captured, distance between the user whose iris image is captured and the user terminal 100, shape of an eye in the iris image, and/or neighboring color of the user in the capturing of the iris image as the capturing condition.

The output unit 130 may be configured to output a variety of content provided from the user terminal 100. The output unit 130 may include a display 131 and/or a speaker 132. The display 131 may be configured to display various images and UIs. The display 131 may display a captured image or a received image. The display 131 may display the various UIs through control of the controller 140. For example, if the user terminal 100 is unlocked via successful iris recognition, the display 131 may display a UI configured to provide a determined physical condition result. The UI configured to provide the physical condition result may include a UI configured to notify the user of a health problem, a UI configured to notify the user of a hospital located within a preset distance from the user terminal 100, and/or a self-diagnosis UI.

The speaker 132 may be configured to output audio data. The speaker 132 may be configured to output a variety of audio data processed in an audio processor (not shown) as well as various notification sounds and voice messages. For example, if the iris recognition is successful, the speaker 132 may output a tone to notify the user of the iris recognition success and unlocking of the user terminal 100. The speaker 132 may include an audio terminal. The various audio notifications output through the speaker 132 may be merely exemplary, and the notification may be output as a vibration type, or as a light-emitting type by a light emitting diode (LED).

The detector 150 may include a plurality of sensors and a camera and may detect a surrounding environment of the user terminal 100 and a capturing condition for when an iris image is captured. For example, the detector 150 may include a sensor module 151, a camera 152, and a time of flight (TOF) camera 153.

The sensor module 151 may include a plurality of sensors. For example, the sensor module 151 may include sensors such as, for example, a gesture sensor, a gyro sensor, a pressure sensor, an illumination sensor, proximity sensor, and/or an acceleration sensor.

The illumination sensor may detect illumination of an environment in which the user terminal 100 is located. That is, when the iris image is captured, the illumination sensor may determine the brightness to determine whether the brightness of an environment in which the pre-stored iris image was captured is similar to the brightness of an environment in which current iris image capture is being performed.

The camera 152 may be configured to capture an image. For example, the camera 152 may capture the iris image of user who is subject to the iris recognition. The TOF camera 153 may be configured to measure a distance between the user terminal 100 and the user. The distance between the user terminal 100 and the user may be calculated based, for example, on the relative positions of facial features of the user. Accordingly, the TOF camera 153 may be able measure the distance between the user terminal 100 and the user who is subject to the iris recognition.

The communication unit 160 may be configured to perform communication with various types of external apparatuses using various types of communication methods. The communication unit 160 may include communication chips such as, for example, a WIFI chip, a Bluetooth chip, an NFC chip, a wireless communication chip, and an infrared (IR) chip. For example, the WIFI chip, the Bluetooth chip, the NFC chip, and the IR chip may perform communication using a WIFI standard, a Bluetooth standard, an NFC standard, and an IR standard, respectively. The NFC chip may be configured to operate according to an NFC standard using a frequency of 13.56 MHz from among the various radio frequency identification (RF-ID) frequency bands such as 135 kHz, 13.56 MHz, 433 MHz, 860 to 960 MHz, and 2.45 GHz.

If the WIFI chip or the Bluetooth chip is used, the communication unit 160 may first transmit/receive a variety of connection information such as a service set identifier (SSID) and a session key, perform communication connection using the connection information, and transmit/receive a variety of information. The wireless communication chip may be a chip configured to perform communication according to one or more of various communication standards, such as Institute of Electrical and Electronics Engineers (IEEE), ZigBee, 3rd generation (3G), 3rd Generation Partnership Project (3GPP), or Long Term Evolution (LTE).

The input unit 170 may receive a user command. The input unit 170 may receive the user command for controlling an overall operation of the user terminal 100. The input unit 170 may be implemented with a remote controller including a four-way (for example, up, down, left, and right) key and an OK key, but this is merely exemplary. The input unit 170 may be implemented with various types of input devices such as, for example, a touch screen, a mouse, a pointing device, and the like. The input unit 170 may also receive a user command by the user's voice. That is, the input unit 170 may include a component such as a microphone to receive the user's voice.

The controller 140 may control an overall operation of the user terminal 100. For example, the controller 140 may determine a capturing condition of the iris image, and convert the iris image to an iris code. The controller 140 may perform iris recognition by comparing the converted iris code to an iris code corresponding to the capturing condition from among the iris codes pre-registered in the storage unit 120.

A method of converting the acquired iris image to an iris code will now be described with reference to FIGS. 11A to 11D.

Figure 11A:
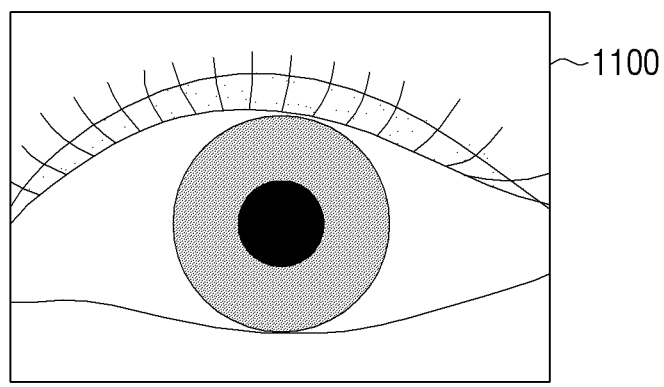
FIGS. 11A to 11D are diagrams illustrating an iris code extracting method according to an exemplary embodiment.

When the iris image 1100 is acquired as illustrated in FIG. 11A, the controller 140 may perform a pretreatment process for generating an iris code. For example, the controller 140 may perform a noise removing process to remove elements unnecessary for iris recognition in the iris image 1100. The controller 140 may perform normalization on the iris image 1100 by detecting a boundary of an iris using a circular boundary detector and converting the iris region to a polar coordinate system.

Figure 11B:
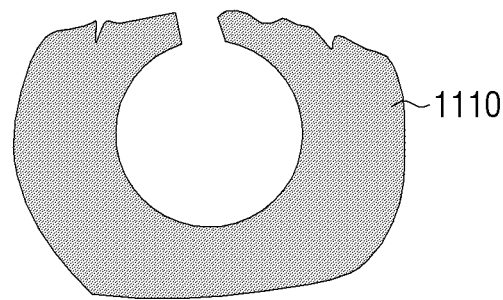
Figure 11C:
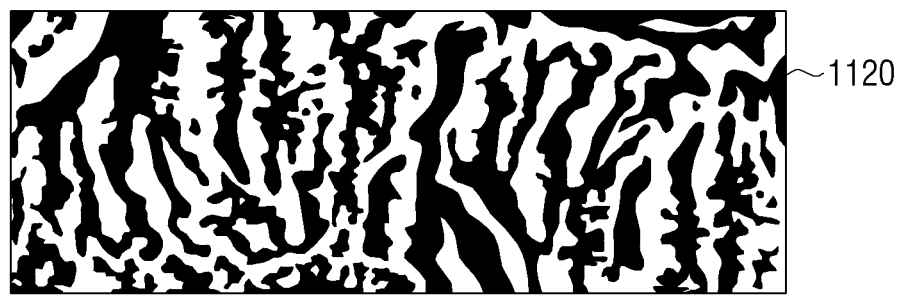
Figure 11D:
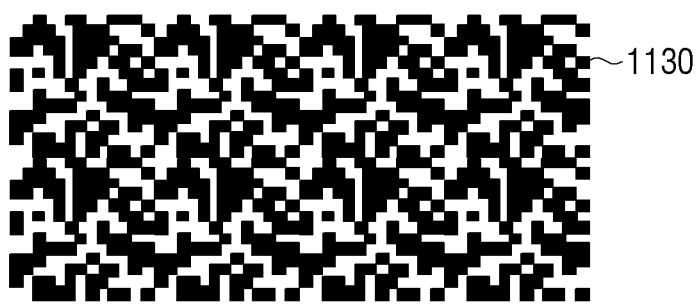

The controller 140 may separate the iris region 1110 illustrated in FIG. 11B from the iris image 1100 through the above-described method. The controller 140 may convert the separated iris region 1110 to a pattern 1120 as illustrated in FIG. 11C by normalizing the separated iris region 1110 to a rectangular shape and extracting a feature of an enquiry pattern of the iris region 1110. The controller 140 may generate an iris code 1130 as illustrated in FIG. 11D and store the generated iris code 1130. The controller 140 may also determine a physical condition of the user based on the iris recognition matching rate for the generated iris code 1130.

The iris recognition matching rate may refer to a percentage match between the generated iris code 1130 and a stored iris code. If the generated iris code matches a stored iris code by a matching percentage greater than a minimum threshold, the iris recognition is considered to be successful and the user terminal 100 will be unlocked for the user's use. If the matching rate is less than or equal to the minimum threshold, the controller 140 will not unlock the user terminal 100.

When the user fails iris recognition, the controller 140 may authenticate the user with a password to unlock the user terminal 100. The controller 140 may then determine the physical condition of the user based on the iris image acquired for iris recognition, as well as other images that may be acquired after unlocking the user terminal 100.

Accordingly, regardless of whether the iris recognition was successful, the controller 140 may control taking a measurement of a pupil cycle time (PCT) of the user. If the measured pupil cycle time is not within a range of the preset pupil cycle time, the controller 140 may determine the physical condition of the user. That is, if the measured pupil cycle time is smaller or larger than a preset range for the pupil cycle time, regardless of the iris recognition matching rate, the controller 140 may recognize that the health of the user is not normal and determines the physical condition of the user.

The iris image may be acquired through the iris image acquisition unit 110 and the acquired iris image may be analyzed to generate an iris code. The iris code may be stored (registered) in the storage unit 120, and the controller 140 may store in the storage unit 120 information related to the iris image and the capturing condition of the iris image. The information may include the pupil cycle time measured in the iris image acquisition and the iris code converted from the iris image in addition to the iris image.

The capturing condition may include an illumination value (brightness) of the environment in which the iris image was captured, the distance between the user and the user terminal 100, shape of the eye of the user in the image taken for the iris authentication, and/or a neighboring color of the user. These capturing conditions may be acquired by the detector 150 when the iris image is acquired If the iris image is acquired through the iris image acquisition unit 110 and the acquired iris image is registered as the iris code, the controller 140 may match the iris code to the capturing condition of the iris image detected through the detector 150 and store the matching result in the storage unit 120.

When the iris recognition being performed by acquiring the iris image, the controller 140 may determine the capturing condition during the performing of the iris recognition. The controller 140 may acquire a preset iris image corresponding to the capturing condition determined in the capturing condition stored in the storage unit 120, and control the physical condition to be determined based on the pre-stored iris image.

That is, the controller 140 may remove an eyelid region and the reflection region included in the acquired iris image, and determine an iris disease of the physical condition by comparing the iris image which the eyelid region and the reflection region are removed therefrom and the pre-stored iris image.

Figure 3A:
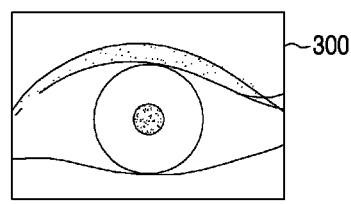
FIGS. 3A and 3B are diagrams illustrating a method of detecting an iris region according to an exemplary embodiment.
Figure 3B:
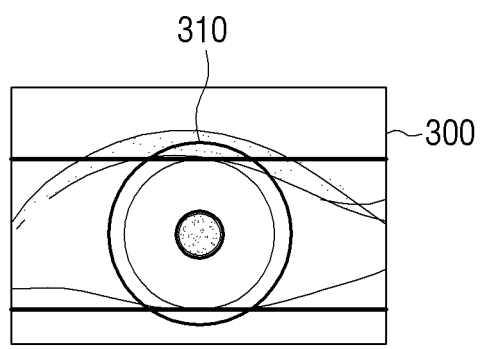

For example, when an iris image 300 is acquired as illustrated in FIG. 3A, the controller 140 may control the process of acquiring the iris region 310 by separating the iris in the iris image 300 as illustrated in FIG. 3B. The controller 140 may acquire the iris image 300 that is not covered by the eyelid. When the iris image 300 is captured, the image may also include a reflection region from light being reflected by an external element such as eye glasses. Therefore, the controller 140 may control detection of the light reflection region and removal of that region.

The storage unit 120 may have pre-stored in it images for eyes with various abnormal symptoms. The controller 140 may compare the iris image 300 with the eyelid region and the light reflection region removed with a plurality of images pre-stored in the storage unit 120. When an image similar to the iris image 300 is found, the controller 140 may be able to suggest the specific disease that the user may have in their iris.

The controller 140 may acquire an illumination value of an environment when the iris image 300 is captured through an illumination sensor as part of the capturing condition as described above.

The controller 140 may compare a pupil cycle time acquired during the capturing of the iris image with a pupil cycle time for a pre-stored iris image. That is, the controller 140 may be able to determine if the physical condition of the user is not normal based on the acquired pupil cycle time not being within a range of the pre-stored pupil cycle time.

The controller 140 may acquire a distance between the user terminal 100 and the user as a capturing condition.

Figure 4A:
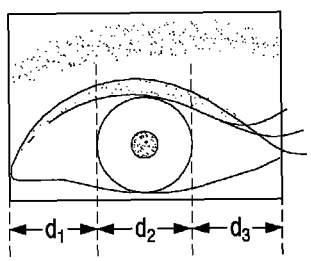
FIGS. 4A and 4B are diagrams illustrating a method of measuring a distance between a user terminal and a user according to an exemplary embodiment.
Figure 4B:
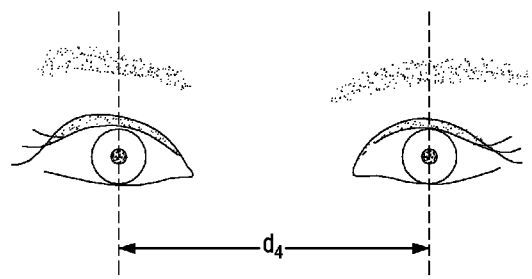

FIGS. 4A and 4B are diagrams illustrating a method of acquiring the distance between the user terminal 100 and the user.

For example, as illustrated in FIG. 4A, the controller 140 may acquire the distance between the user terminal 100 and the user based on lengths d1 and d3 from both ends of an eye to an iris and a lateral length d2 of the iris. In another example, as illustrated in FIG. 4B, the controller 140 may acquire the distance between the user terminal 100 and the user based on a length d4 between the two eyes. In this example, the length d4 between the two eyes may be smaller when the user is farther away from the user terminal 100 than when the user is closer to the user terminal 100.

As described above, when the TOF camera 153 is included in the detector 150, the controller 140 may acquire the distance between the user terminal 100 and the user using the TOF camera 153.

The controller 140 may control the output unit 130 to output the determined physical condition. For example, the output unit 130 may output the physical condition as image content and/or audio content. Hereinafter, an example in which the output unit 130 includes the display 131 and outputs the physical condition in an image content type such as a UI through the display 131 will be described.

If a disease in the user's eye is determined through the above-described method, the controller 140 may control the display 131 to display a UI to notify the user of the disease. For example, the controller 140 may control the display 131 to display the physical condition by displaying the determined physical condition on an image that has a facial region including an eye of the user.

The controller 140 may display a self-diagnosis UI for allowing the user to determine detailed information of the disease through self-diagnosis. If the physical condition of the user is determined to be poor according to the self-diagnosis result, the controller 140 may control the display 131 to display a UI to notify the user of a hospital located within a preset distance from the user terminal 100. Detailed information for the self-diagnosis UI and the UI for notifying the user of the hospital will be described later.

Accordingly, the user may perform iris recognition to unlock the user terminal 100 and simultaneously check their physical condition via the user terminal 100 as described above. Hereinafter, a method of determining a physical condition by performing iris recognition and a method of displaying a UI according to the determination result will be described in detail.

FIGS. 5A to 5D are diagrams illustrating an iris recognition method according to an exemplary embodiment.

Figure 5A:
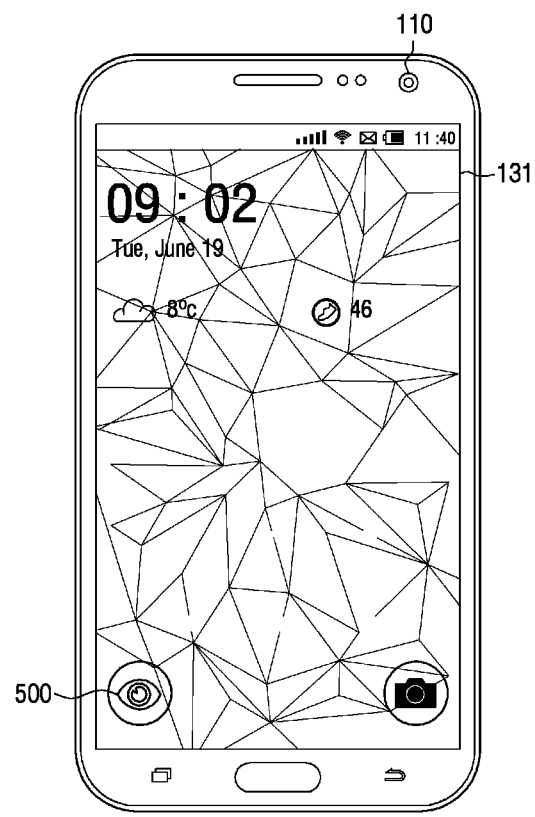
FIGS. 5A to 5D are diagrams illustrating a method of unlocking a user terminal using iris recognition according to an exemplary embodiment.

FIG. 5A is a diagram illustrating the user terminal 100 that is locked and an initial screen is displayed. FIG. 5A has illustrated a smart phone as the user terminal 100, but the user terminal 100 is not limited to the smart phone. The user terminal 100 may be an electronic apparatus that can be unlocked by iris recognition. For example, the user terminal 100 may be one of various electronic apparatuses such as a portable phone, a laptop PC, a tablet PC, a television (TV), a large format display (LFD), a digital camera, a camcorder, a personal digital assistant (PDA), a smart watch, smart glasses, and the like.

As illustrated in FIG. 5A, the user terminal 100 may include the iris image acquisition unit 110 and the display 131. The user terminal 100 that is locked may display an iris recognition UI 500. The user may select the iris recognition UI using a stylus pen, a finger, another body part of the user, or the like.

Figure 5B:
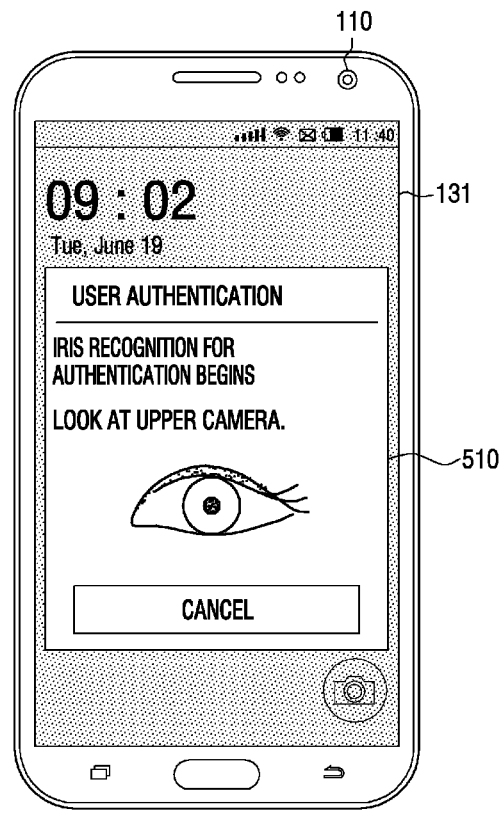
Figure 5C:
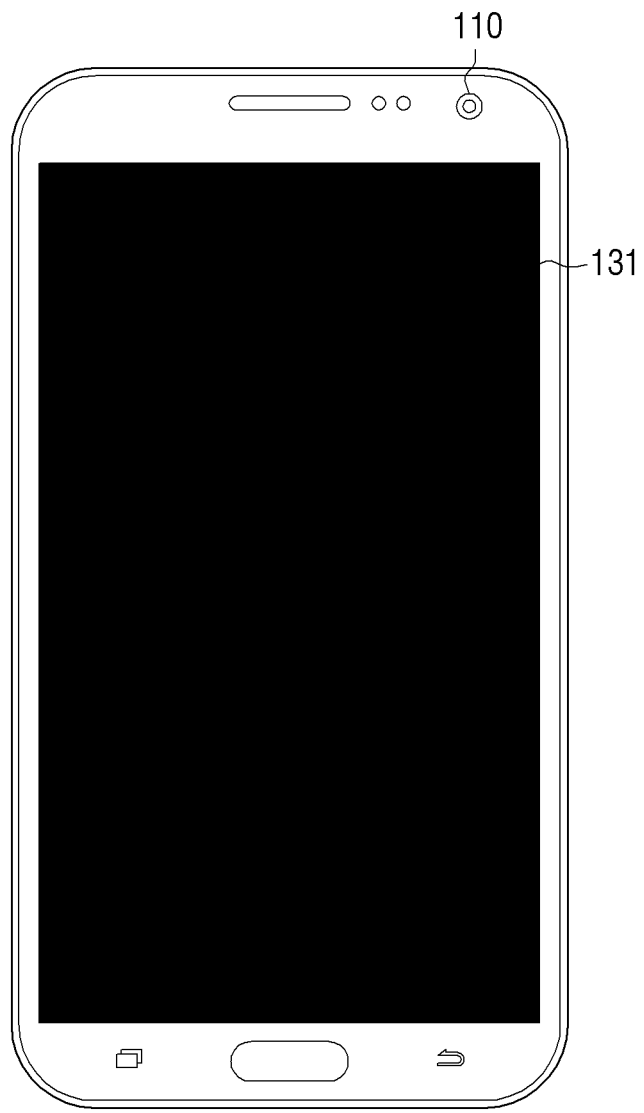

FIG. 5B is a diagram illustrating the user terminal 100 that displays the UI 510 when the iris recognition UI 500 is selected by the user. The user terminal 100 may instruct the user to look at the iris image acquisition unit 110 of the user terminal 100 and to perform image capturing through the iris recognition UI 500. As shown in FIG. 5C, the user terminal 100 may turn off the display 131 while acquiring the iris image of the user with the iris image acquisition unit 110. That is, while the iris of the user is captured, the controller 140 may turn off the display 131 to minimize effects from lights shining from the display 131.

Figure 5D:
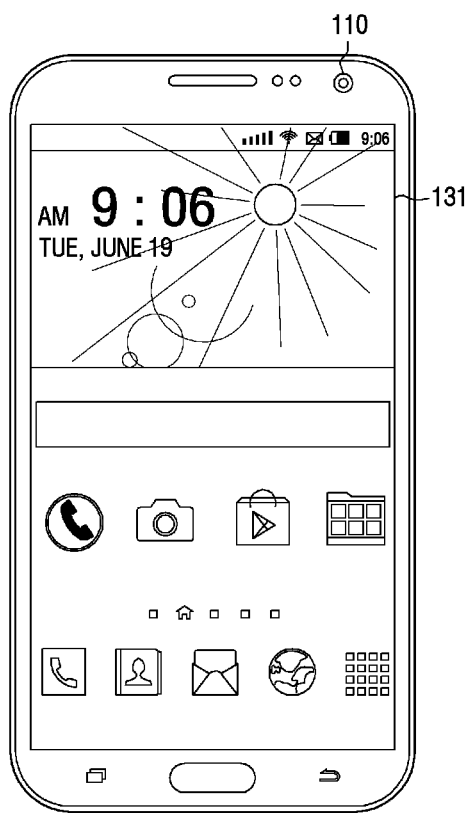

When the iris of the user is recognized, the controller 140 may control the display 131 to unlock the user terminal 100 and display a home screen of the user terminal 100 as illustrated in FIG. 5D. For example, the controller 140 may detect an iris region from the acquired image and generate an iris code by normalizing the detected iris region to a rectangular shape. The controller 140 may perform masking on a region of the normalized rectangular iris code that is covered with an eyebrow or an eyelid, and may perform iris recognition of the user by comparing the remaining region of the iris code.

The controller 140 may register the iris image for the iris recognition by the user. That is, the controller 140 may generate the iris code by analyzing the iris image according to the user and control the storage unit 120 to store the iris code. The controller 140 may also match the capturing condition to the iris image and store the matching result. The controller 140 may match the iris image, the iris code captured from the iris image, and the pupil cycle time to the capturing condition and store the matching result.

While the iris image for iris recognition being acquired, the controller 140 may control the detector 150 to detect various capturing conditions described above. When a capturing condition corresponding to the detected capturing condition among capturing conditions pre-stored in the storage unit 120 is determined, the controller 140 may perform the iris recognition for the acquired iris image using an iris code corresponding to the determined capturing condition.

When an iris recognition matching rate is within a preset range, the controller 140 may determine the physical condition of the user who is subject to the iris recognition based on the iris recognition result. For example, if the iris recognition matching rate is less than or equal to a preset threshold value, the controller 140 may determine the physical condition of the user based on the iris image. For example, the controller 140 may determine the physical condition of the user when the iris recognition matching rate is less than 95%.

Figure 6A:
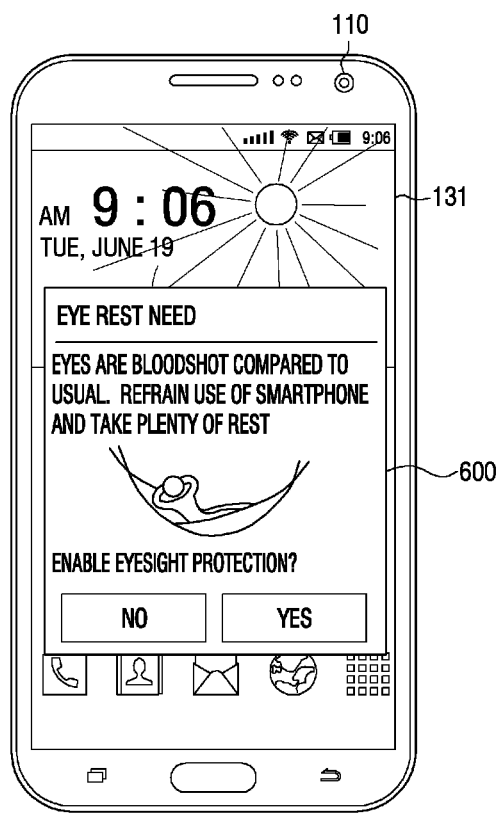
FIGS. 6A to 6C are diagrams illustrating physical condition determination result user interfaces (UIs) according to various exemplary embodiments.
Figure 6B:
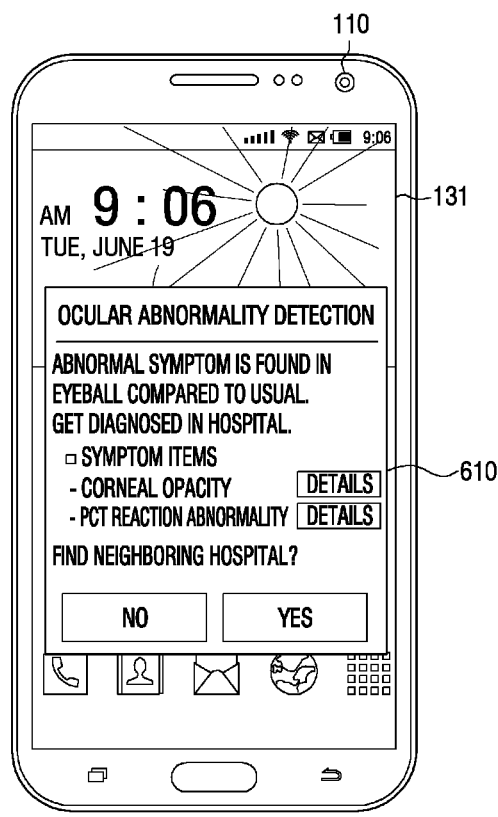
Figure 6C:
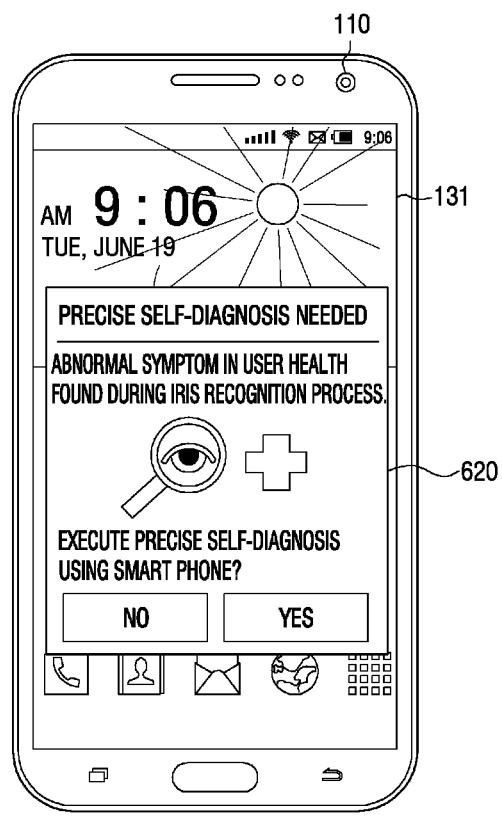

When the iris recognition is successful, the controller 140 may control the display 131 to display determination result UIs 600, 610, and 620 as illustrated in FIGS. 6A to 6C.

The controller 140 may control the pupil cycle time (PCT) to be measured, and if the measured pupil cycle time is not within a preset range for the pupil cycle time, the controller 140 may determine the physical condition of the user who is subject to the iris recognition. That is, the controller 140 may measure the pupil cycle time regardless of the iris recognition matching rate. If the measured pupil cycle time is not within the preset range of the previous pupil cycle time of the user, the controller 140 may determine the physical condition of the user who is subject to the iris recognition.

The controller 140 may determine the physical condition of the user in units of preset iris recognition number of times regardless of the capturing condition. The controller 140 may determine the physical condition of the user in response to the user being determined to enter a preset position.

The controller 140 may determine the physical condition of the user in response to the condition the user setup or the initial setup being satisfied. For example, in response to the user terminal 100 being charged or in response to a threshold time being passed after the physical condition of the user is determined, the controller 140 may determine the physical condition of the user.

The controller 140 may control the display 131 to display the determination result UIs 600, 610, and 620 for the physical condition of the user. For example, FIG. 6A is a diagram illustrating the user terminal 100 that displays the determination result UI 600 in response to iris recognition being successful and an abnormal symptom being found as the iris image analysis result. In this example, in response to an eyeball of the user being bloodshot or in response to many capillary being detected in the eyeball of the user as compared with a pre-registered iris image, the controller 140 may control the display 131 to display the determination result UI 600 advising the user to take a rest.

In response to a user command for enabling an eyesight protection function being input through the determination result UI 600, the controller 140 may control the display 131 to protect the eyesight of the user. For example, the controller 140 may control brightness of the display 131 according to detected neighboring illumination.

FIG. 6B is a diagram illustrating the user terminal 100 that displays the determination result UI 610 in response to iris recognition being successful and a relatively serious health symptom being found as the iris image analysis result. For example, in response to a boundary of an iris or an pupil included in the iris image being extremely obscured, in response to a color of the eyeball of the user being not simply bloodshot but being turbidly changed, in response to a shape of the detected iris being different from that of the pre-stored iris, or the iris recognition matching rate being less than or equal to a threshold value (for example, 90%, which is less than the passing threshold of 95% for iris recognition) due to the above-described issues, the controller 140 may determine a disease in the eyeball or iris of the user, and control the display 131 to display the determination result UI 610 including information about the ocular abnormality.

Even in response to a measured pupil cycle time not being within a range of the normal pupil cycle time as described above, the controller 140 may control the display 131 to display the determination result UI 610 including information for informing that the ocular abnormality is found.

In response to a user command to search for a neighboring hospital being input through the determination result UI 610, the controller 140 may search for a hospital located within a preset distance from the user terminal 100, and control the display 131 to display a hospital list UI according to the search result.

FIG. 6C is a diagram illustrating the user terminal 100 that displays the determination result UI 620 in response to iris recognition being successful and a serious health symptom being found. For example, in response to the iris recognition matching rate being approximately only 50% and thus failing repeatedly, the controller 140 may determine that the low matching rate may be a result of serious health abnormality in the eyeball of the user. The controller 140 may control the display 131 to display the determination result UI 620 including information that self-diagnosis is needed since the serious ocular abnormality is found. In response to a user command for executing self-diagnosis being input through the determination result UI 620, the controller 140 may control the display 131 to display a self-diagnosis UI. The detailed self-diagnosis UI will be described later with reference to FIGS. 8A to 8L.

Figure 7A:
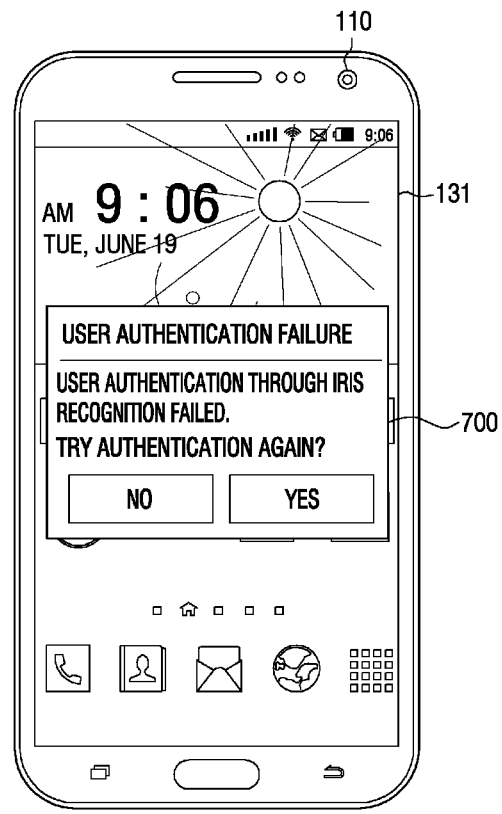
FIGS. 7A and 7B are diagrams illustrating iris recognition failure screens according to various exemplary embodiments.
Figure 7B:
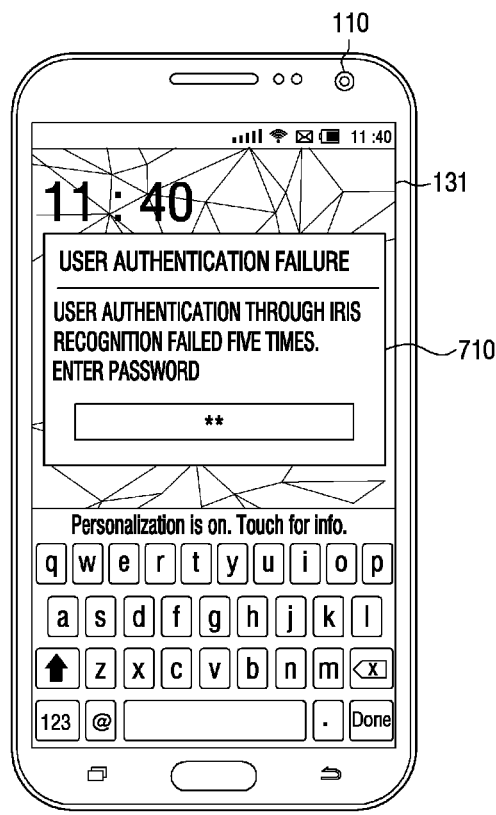

FIGS. 7A and 7B are diagrams illustrating the user terminal 100 in response to failing iris recognition. That is, in response to failing iris recognition, the controller 140 may control the display 131 to display an authentication failure UI 700 as illustrated in FIG. 7A. The user terminal 100 may notify the user of the user authentication failure through the authentication failure UI 700, and may receive a user command for whether to try iris recognition again.

As illustrated in FIG. 7B, the controller 140 may control the display 131 to display a password input UI 710. That is, the controller 140 may notify the user of the failure of iris recognition a preset number of times and give the user a chance to enter a password through the password input UI 710. Accordingly, even though iris recognition failed, the controller 140 may unlock the user terminal 100 through a separate method.

FIGS. 8A to 8L are diagrams illustrating self-diagnosis UIs according to various exemplary embodiments. The controller 140 may control the display 131 to display various types of self-diagnosis UIs that allows the user to find information for a specific disease through self-diagnosis.

Figure 8A:
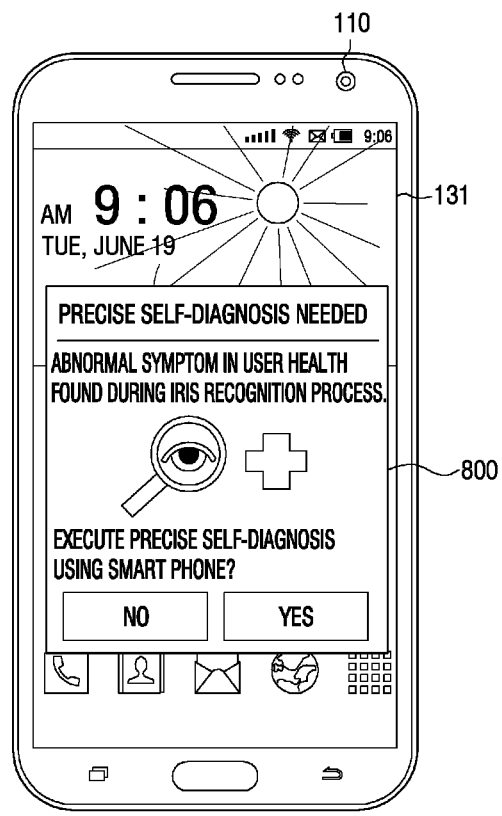
FIGS. 8A to 8L are diagrams illustrating self-diagnosis UIs according to various exemplary embodiments.

As described above, in response to the iris recognition matching rate being lower than a preset iris recognition matching rate, in response to the measured pupil cycle time not being within a range of the normal pupil cycle time, or in response to failing iris recognition and unlocking the user terminal 100 through another method, the controller 140 may control the display 131 to display a self-diagnosis UI 800 as illustrated in FIG. 8A. That is, the user terminal 100 may inform the user that ocular abnormality of the user has been found and propose to the user to execute the self-diagnosis UI 800.

Figure 8B:
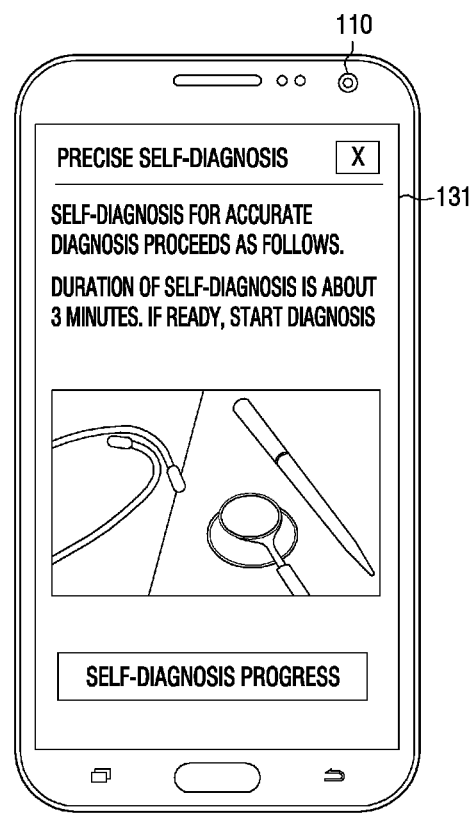
Figure 8C:
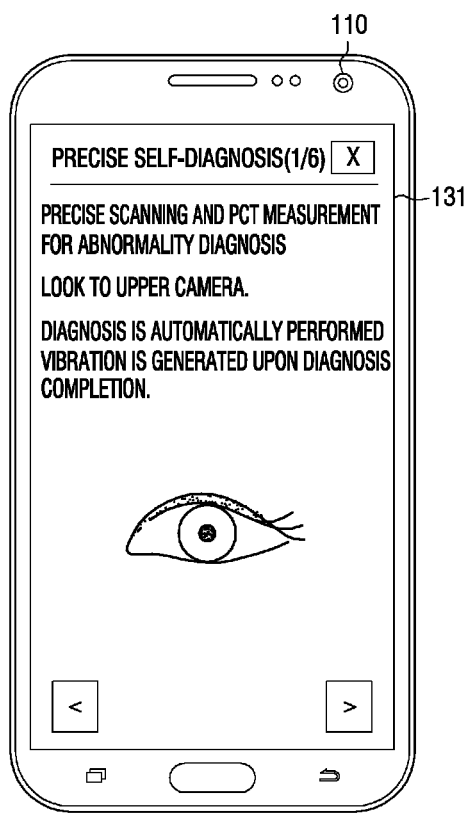
Figure 8D:
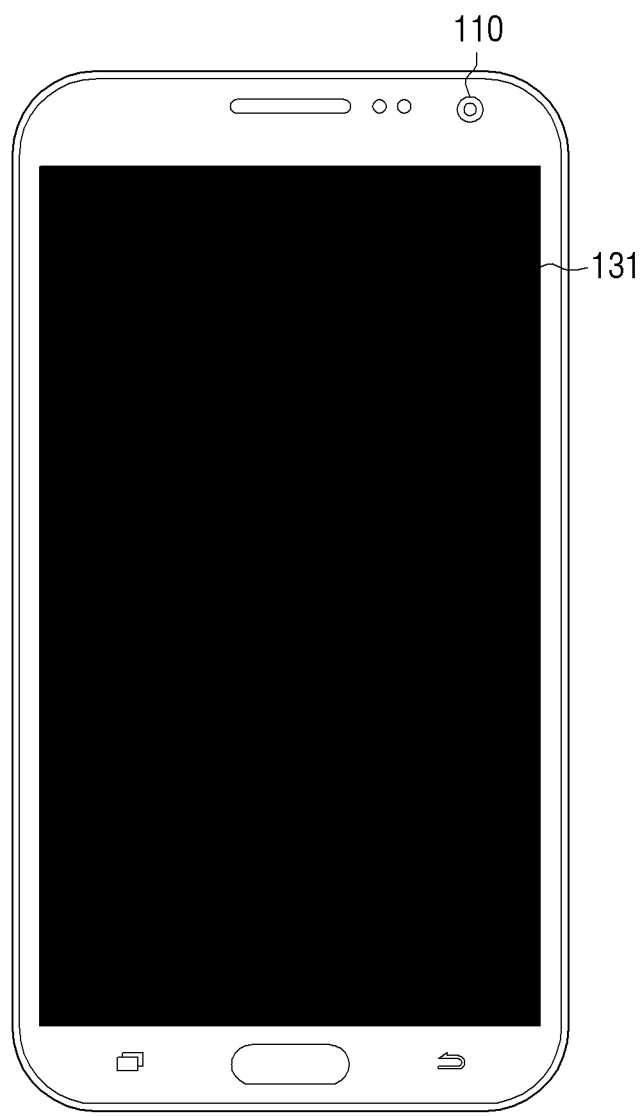

FIGS. 8B to 8D are diagrams illustrating the user terminal 100 that displays self-diagnosis guidelines in response to a user command for executing the self-diagnosis being input through the self-diagnosis UI 800. As illustrated in FIG. 8B, the user terminal 100 may notify the user of execution of a self-diagnosis routine.

As illustrated in FIG. 8C, the controller 140 may control the display 131 to display a guideline UI for acquiring an iris image for self-diagnosis. While the iris image of the user is acquired through the iris image acquisition unit 110, as illustrated in FIG. 8D, the controller 140 may control the display 131 to be turned off. That is, while the iris image is acquired, the display 131 may be turned off to minimize the effect of light from the display 131. Some embodiments may omit the guideline UIs illustrated in FIGS. 8C and 8D.

Figure 8E:
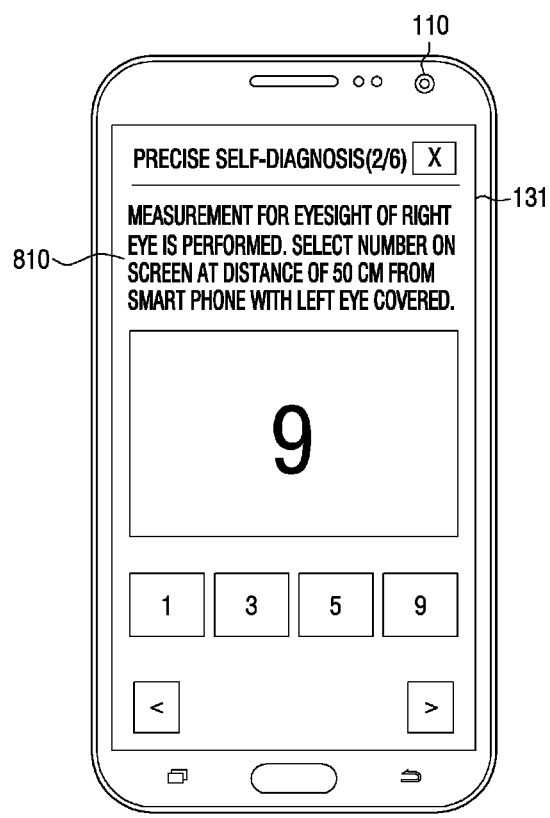

FIG. 8E is a diagram illustrating the user terminal 100 that displays an eyesight test UI 810 for measuring an eyesight of the user during the self-diagnosis. The user may locate the user terminal 100 to a certain distance and determine whether the user is able to see the number displayed in the eyesight test UI 810, and thus the user's eyesight may be measured through the eyesight test UI 810. The user may select the number displayed in the eyesight test UI 810 using an external control apparatus (not shown) configured to control the user terminal 100.

Figure 8F:
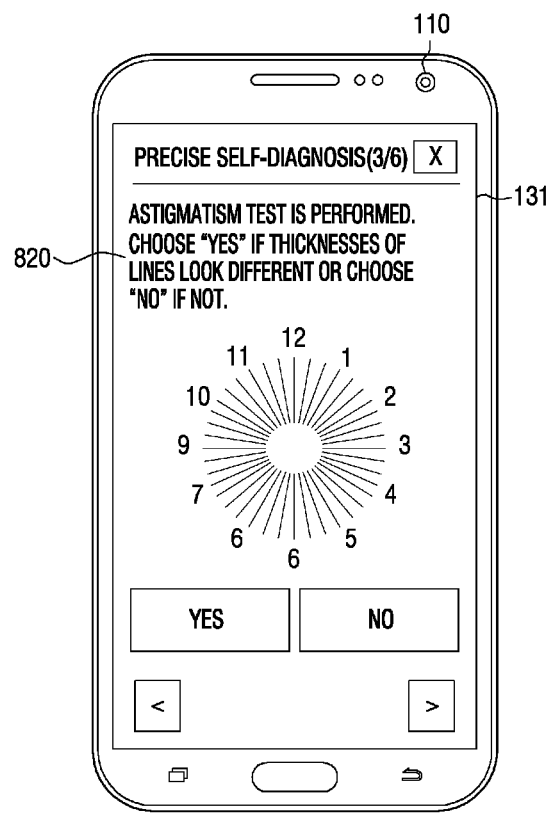

FIG. 8F is a diagram illustrating the user terminal 100 that displays an astigmatism test UI 820 for determining astigmatism during the self-diagnosis. The user terminal may determine the astigmatism of the user by the user's answer to a question for the astigmatism test displayed in the astigmatism test UI 820.

Figure 8G:
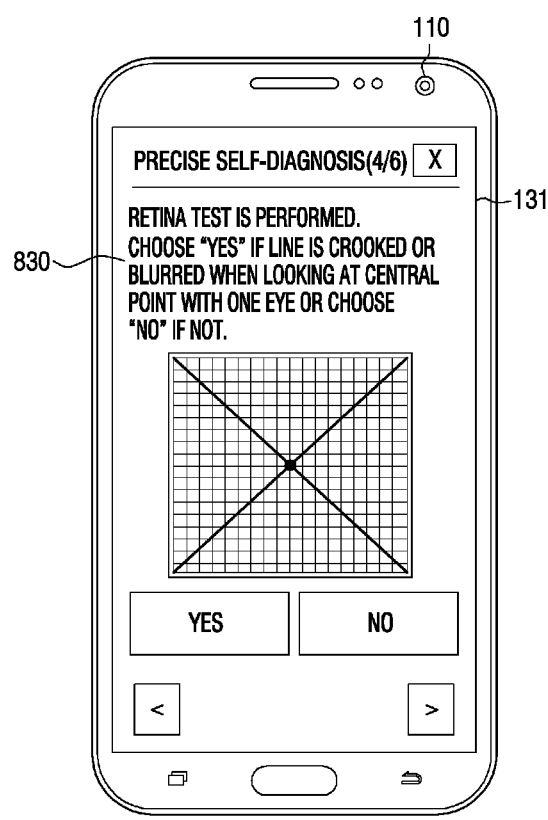

FIG. 8G is a diagram illustrating the user terminal 100 that displays a retina test UI 830 for determining astigmatism during the self-diagnosis. The user terminal may determine whether the retinal of the user is abnormal by the user's answer to a question for the retinal test displayed in the retina test UI 830.

Figure 8H:
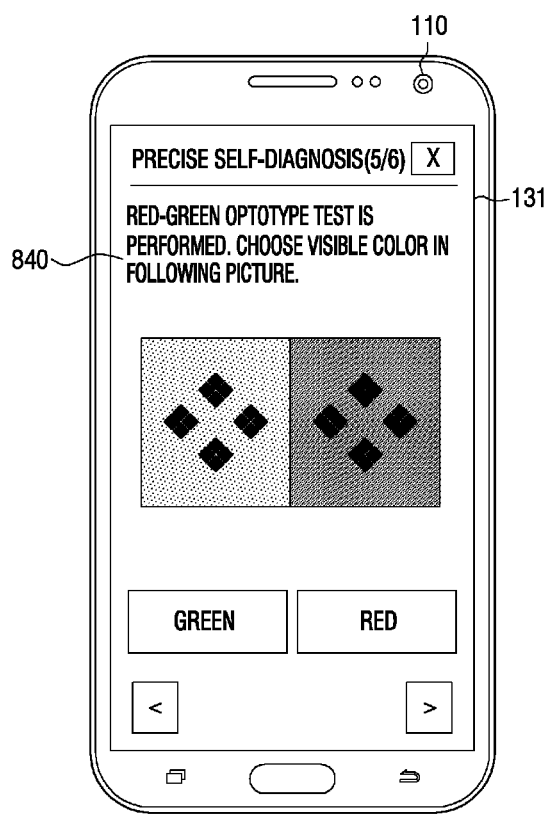
Figure 8I:
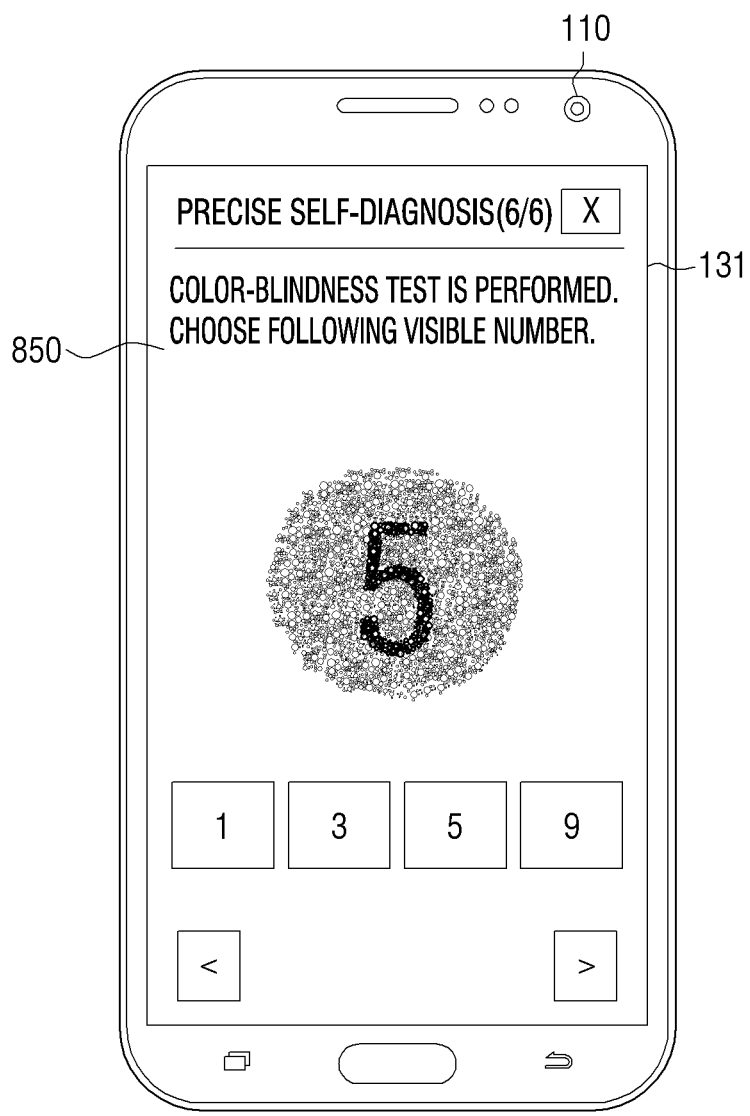

FIGS. 8H and 8I are diagrams illustrating the user terminal 100 that displays color-blindness test UIs 840 and 850 for determining color blindness or red-green blindness during the self-diagnosis.

As illustrated in FIG. 8H, the user terminal 100 may determine red-green blindness of the user through the color-blindness test UI 840 for red-green optotype test. As illustrated in FIG. 8I, the user terminal 100 may determine color blindness of the user through the color-blindness test UI 850 for determining color-blindness.

Figure 8J:
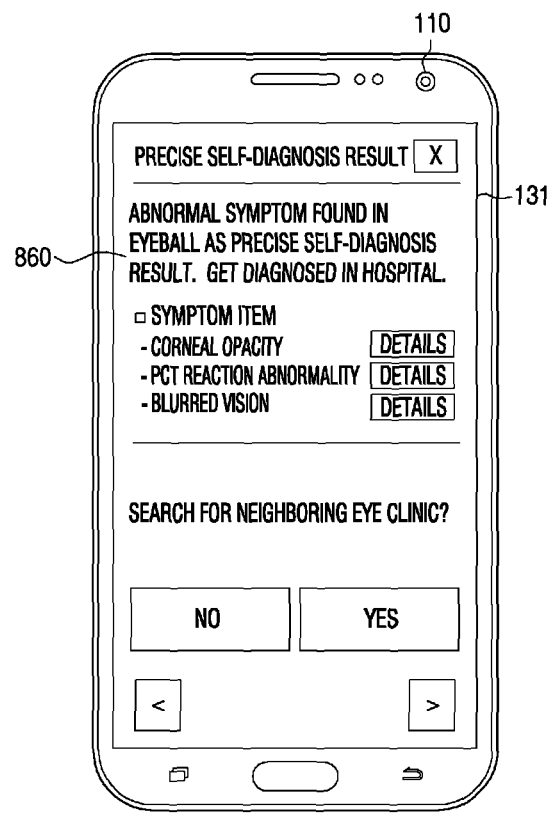

FIG. 8J is a diagram illustrating the user terminal 100 that displays a self-diagnosis result UI 860 according to an exemplary embodiment. Results of the self-diagnosis tests such as the above-described methods and the like may be analyzed, and the user terminal 100 may provide information for a suspected disease through the self-diagnosis result UI 860.

The user terminal 100 may measure the pupil cycle time even without separate self-diagnosis. If the measured pupil cycle time is not within the normal pupil cycle time range, the user terminal 100 may inform the user that the measured pupil cycle time is not within the normal range through the self-diagnosis result UI 860.

Figure 8K:
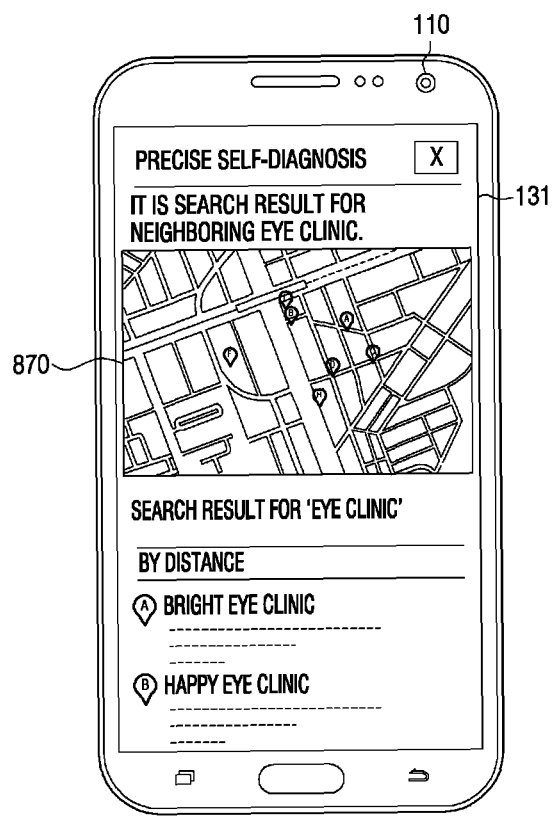

The user terminal 100 may receive a user command for searching for a hospital located within a preset distance from the position of the user terminal 100 through the self-diagnosis result UI 860. In response to the user command to search for the hospital, the user terminal 100 may display a hospital search result UI 870 as illustrated in FIG. 8K. According to an exemplary embodiment, the user terminal 100 may transmit the self-diagnosis result to the hospital.

Figure 8L:
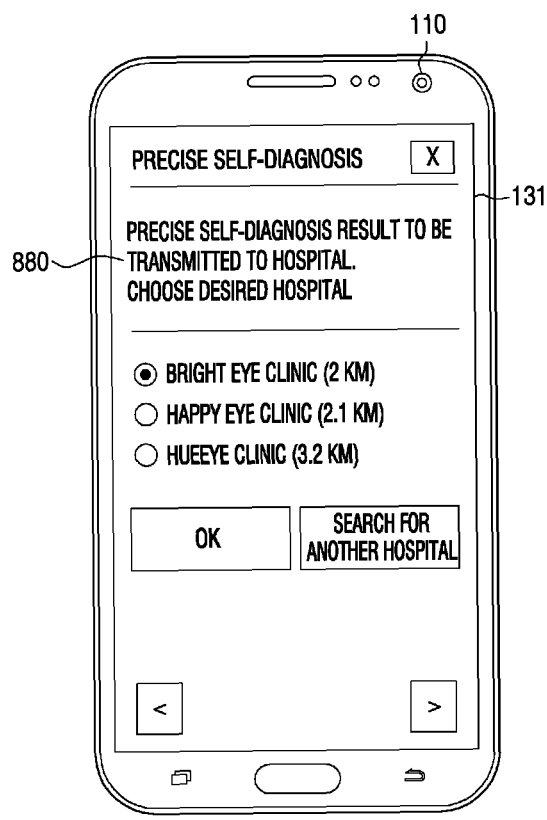

As illustrated in FIG. 8L, the controller 140 may display a UI 880 for receiving a user command for selecting a hospital to which the self-diagnosis result is to be transmitted. Even if the user command is not input, the controller 140 may control the communication unit 160 to provide the physical condition determination result to a preset hospital according to setup, which may include whenever an abnormal health condition is detected.

Figure 9:
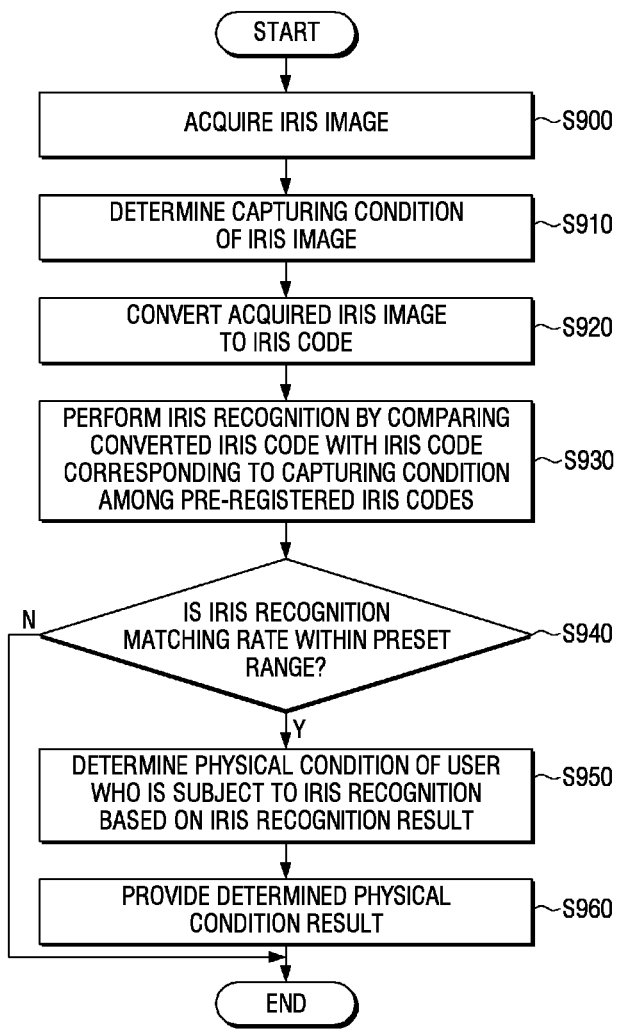
FIG. 9 is a flowchart illustrating a providing method of a user terminal according to an exemplary embodiment.

FIG. 9 is a flowchart illustrating a providing method of the user terminal 100 according to an exemplary embodiment. First, the user terminal 100 may acquire an iris image (S900). The user terminal 100 may acquire the iris image by capturing an iris image of the user or receiving a captured iris image of the user.

The user terminal 100 may determine a capturing condition of the iris image (S910). That is, in iris image registration for iris recognition, the user terminal 100 may determine the capturing condition, match the capturing image to the iris image, and store the matching result. Accordingly, the user terminal 100 may determine the capturing condition of the acquired iris image and may search for a stored iris image with the same or similar capturing condition as the determined capturing condition.

The user terminal 100 may convert the acquired iris image to an iris code (S920), and perform iris recognition by comparing the converted iris code with an iris code corresponding to the capturing condition among pre-registered iris codes (S930). The user terminal 100 may determine whether an iris recognition matching rate is within a preset range (S940).

The iris recognition matching rate within the preset range may refer to an iris recognition matching rate within a range where the user terminal 100 is unlocked. For example, the preset range may refer to a range below a preset matching rate (for example, 95%), but an iris recognition matching rate in that range may be deemed to have passed iris recognition. This may make iris recognition more flexible by allowing the user more leeway with respect to the condition of the user's eyes. However, the user terminal 100 may determine a physical condition for a user with an iris recognition matching rate in the preset range or below.

The user terminal 100 may determine a physical condition of the user who is subject to the iris recognition based on the iris recognition result (S950). That is, the user terminal 100 may detect an iris image corresponding to the acquired iris image by comparing the iris image acquired for the iris recognition with the pre-stored iris images according to various diseases. Accordingly, the user terminal 100 may determine an eye disease of the user using the iris image.

The user terminal 100 may provide the determined physical condition result (S960). For example, in response to unlocking the user terminal 100 after successful iris recognition, the display 131 may display a UI for providing the determined physical condition result.

The UI for providing the physical condition result may include a UI for notifying the user of a health problem, a UI for notifying the user of a hospital located within a preset distance from the user terminal 100, and/or a self-diagnosis UI.

Figure 10:
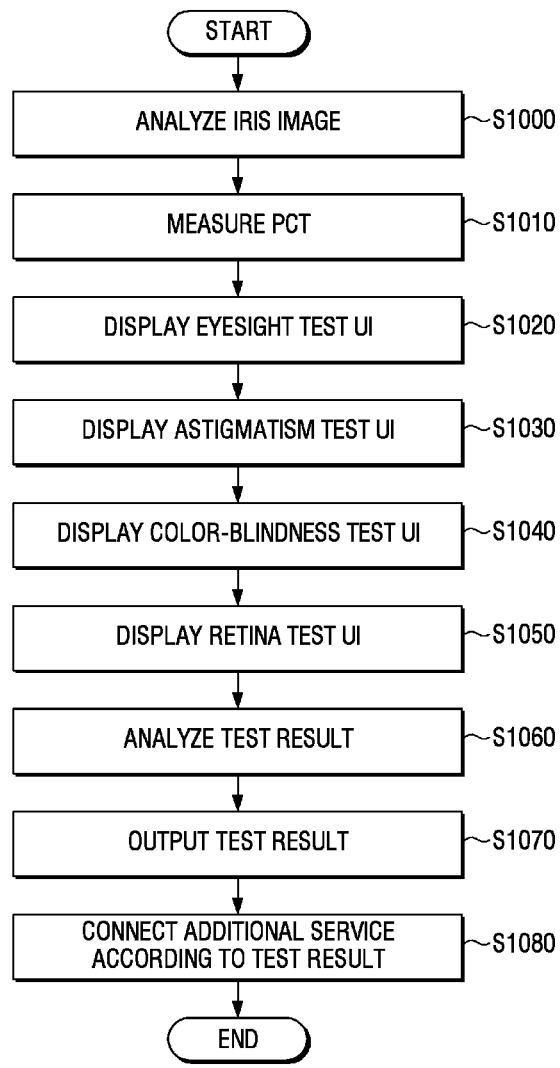
FIG. 10 is a flowchart illustrating a method of measuring a pupil cycle time and providing a self-diagnosis UI according to an exemplary embodiment.

FIG. 10 is a flowchart illustrating a method of measuring a pupil cycle time and providing a self-diagnosis UI according to an exemplary embodiment.

The user terminal 100 may analyze the iris image (S1000), and measure a pupil cycle time (S1010). While the user terminal 100 performs the iris recognition, the user terminal 100 may measure the pupil cycle time and determine whether the measured pupil cycle time is within a normal pupil cycle time range. In response to the measured pupil cycle time not being within the normal pupil cycle time range, the user terminal 100 may display various self-diagnosis UIs.

For example, the user terminal 100 may display an eyesight test UI (S1020) and display an astigmatism test UI (S1030). The user terminal 100 may display a color-blindness test UI for determining red-green blindness or color blindness (S1040). The user terminal 100 may display a retina test UI (S1050).

The display order of the above-described self-diagnosis UIs may be changed according to the user setup or an iris image analysis result. Other diagnosis UIs may be added or a portion of the diagnosis UIs may be omitted.

The user terminal 100 may analyze a test result (S1060), and output the test result (S1070). That is, the user terminal 100 may determine a problem such as an eye disease or blurred vision of the user and output the test result.

The user terminal 100 may perform additional service according to the test result (S1080). For example, the user terminal 100 may search for a hospital located within a range based on a position of the user terminal 100 and display a hospital list UI according to the search result.

The user terminal 100 may transmit the test result to a hospital in response to a user input or as preset.

Through the providing method of the user terminal 100 as described above, the user may unlock the user terminal 100 using iris recognition and the user terminal 100 may perform a physical examination of the user's eye to give the physical examination result.

The components of the user terminal 100 may be implemented with software. For example, the user terminal 100 may further include a flash memory or other nonvolatile memories. Programs corresponding to the components of the user terminal 100 may be stored in the nonvolatile memory.

The controller of the user terminal may be implemented in a form including a central processing unit (CPU) and a random access memory (RAM). The CPU of the controller may copy the programs stored in the nonvolatile memory into the RAM and perform a function of the user terminal described above by executing the copied programs.

The controller may be configured to control the apparatus in general. The controller may be used with the same meaning as a CPU, a microprocessor, a processor, and the like. The controller of the user terminal may be implemented with a system-on-a-chip or a system on chip (SoC) together with other function units such as the communication unit included in the user terminal.

The providing method of the user terminal according to the above-described various exemplary embodiments may be coded in software and stored in a non-transitory recordable medium. The non-transitory readable medium may be installed in various apparatuses.

The non-transitory readable medium is not a medium configured to temporarily store data such as a register, a cache, or a memory but an apparatus-readable medium configured to permanently or semi-permanently store data. For example, the non-transitory apparatus-readable medium may include a compact disc (CD), a digital versatile disc (DVD), a hard disc, a Blu-ray disc, a memory card, or a read only memory (ROM).

The foregoing exemplary embodiments and advantages are merely exemplary and are not to be construed as limiting the present disclosure. The present teaching can be readily applied to other types of apparatuses. Also, the description of the exemplary embodiments of the present disclosure is intended to be illustrative, and not to limit the scope of the claims, and many alternatives, modifications, and variations will be apparent to those skilled in the art.

What is claimed is:

1. A providing method of providing information to a user of a user terminal, the method comprising:
   capturing, by a camera, an iris image of a user;
   identifying, by a processor, a capturing condition of the iris image;
   converting, by the processor, the iris image to an iris code;
   performing, by the processor, iris recognition by comparing a pre-registered iris code stored in a memory corresponding to the capturing condition of the captured iris image and the converted iris code;
   calculating, by the processor, an iris recognition matching rate in a process of performing the iris recognition by a processor;
   identifying, by the processor, a physical condition of the user who is subject to the iris recognition, in response to the iris recognition matching rate being within a preset rate; and
   displaying an identified physical condition result on a display.

2. The method as claimed in claim 1, wherein identifying the capturing condition includes identifying one or more of an illumination value of an environment in which the iris image is captured, a distance between the user and the user terminal, a shape of an eye in the iris image of the user, and a neighboring color of the user in the capturing of the iris image.

3. The method as claimed in claim 1, further comprising matching, by a processor, information for the iris image to the capturing condition of the iris image and storing a matching result in the memory, wherein identifying the physical condition includes acquiring information for a pre-stored iris image corresponding to the identified capturing condition among pre-stored capturing conditions and identifying the physical condition based on the information for the pre-stored iris image.

4. The method as claimed in claim 1, wherein identifying the physical condition includes identifying the physical condition by removing an eyelid region and a reflection region in the iris image and comparing the iris image with the eyelid region and the reflection region removed and a pre-stored iris image.

5. The method as claimed in claim 1, wherein the iris recognition matching rate being within the preset rate refers to an iris recognition matching rate within a range in which the iris recognition is deemed successful and as a result the user terminal is unlocked.

6. The method as claimed in claim 5, wherein providing the identified physical condition result further includes displaying a user interface (UI) configured to provide the identified physical condition result in response to unlocking the user terminal through success of the iris recognition.

7. The method as claimed in claim 6, wherein the UI configured to provide the identified physical condition result includes one or more of a UI configured to notify the user of a health problem, a UI configured to notify the user of a hospital located within a preset distance from the user terminal, and a self-diagnosis UI.

8. The method as claimed in claim 1, wherein providing the identified physical condition result further includes:
  displaying a self-diagnosis UI configured to allow the user to perform self-diagnosis on the user;
  providing a result of the self-diagnosis performed through the self-diagnosis UI; and
  displaying a UI configured to notify the user of a hospital located within a preset distance from the user terminal in response to the result of the self-diagnosis.

9. The method as claimed in claim 1, wherein performing the iris recognition further includes measuring a pupil cycle time (PCT) of the user, and identifying the physical condition includes identifying the physical condition of the user in response to a measured pupil cycle time not being within a range of a preset pupil cycle time.

10. The method as claimed in claim 1, wherein acquiring the iris image further includes capturing a region including an eye of the user, and providing the identified physical condition result further includes displaying the identified physical condition with a captured image of an eye of the user.

11. A user terminal comprising:
  a camera;
  a memory;
  a display; and
  a processor configured to:
    control the camera to capture an iris image of a user;
    control the memory to store the captured iris image, an iris code, and a capturing condition;
    identify the capturing condition of the iris image;
    convert the iris image to the iris code;
    perform iris recognition by comparing a pre-registered iris code stored in a memory corresponding to the capturing condition of the captured iris image and the converted iris code;
    calculate an iris recognition matching rate;
    in response to the iris recognition matching rate being within a preset rate, identify a physical condition of the user who is subject to the iris recognition; and
    control the display to display an identified physical condition result.

12. The user terminal as claimed in claim 11, further comprising a detector including one or more of a plurality of sensors and a camera, wherein the processor identifies the capturing condition by identifying one or more of an illumination value of an environment in which the iris image is captured, a distance between the user and the user terminal, a shape of an eye in the iris image of the user, and a neighboring color of the user in capturing the iris image through the detector.

13. The user terminal as claimed in claim 11, wherein the processor controls the memory to match information for the iris image to the identified capturing condition of the iris image and store a matching result, and the processor acquires information for a pre-stored iris image corresponding to the identified capturing condition among pre-stored capturing conditions in the memory and identifies the physical condition based on the information for the pre-stored iris image.

14. The user terminal as claimed in claim 11, wherein the processor identifies the physical condition by removing an eyelid region and a reflection region in the iris image and comparing the iris image with the eyelid region and the reflection region removed and a pre-stored iris image.

15. The user terminal as claimed in claim 11, wherein the iris recognition matching rate being within the preset rate refers to an iris recognition matching rate within a range in which the iris recognition is deemed successful as a result the user terminal is unlocked.

16. The user terminal as claimed in claim 15, wherein the processor controls the display to display a user interface (UI) configured to provide the identified physical condition result in response to unlocking the user terminal through success of the iris recognition.

17. The user terminal as claimed in claim 16, wherein the UI configured to provide the identified physical condition result includes one or more of a UI configured to notify the user of a health problem, a UI configured to notify the user of a hospital located within a preset distance from the user terminal, and a self-diagnosis UI.

18. The user terminal as claimed in claim 11, wherein the processor controls the display to display a self-diagnosis UI configured to allow the user to perform self-diagnosis on the user, provide a result of the self-diagnosis performed through the self-diagnosis UI, and display a UI configured to notify the user of a hospital located within a preset distance from the user terminal in response to the result of the self-diagnosis.

19. The user terminal as claimed in claim 11, wherein the processor measures a pupil cycle time (PCT), and identifies the physical condition of the user in response to a measured pupil cycle time being not within a range of a preset pupil cycle time.

20. The user terminal as claimed in claim 11, wherein the processor controls the camera to acquire the iris image by capturing a region including an eye of the user, and controls the display to provide the physical condition result by displaying the identified physical condition with a captured image of an eye of the user.

* * * * *